United States Patent [19]

Davies

[11] Patent Number: 5,210,210
[45] Date of Patent: May 11, 1993

[54] CHIRAL AUXILIARIES AND THEIR USE IN THE SYNTHESIS OF CHIRAL MOLECULES

[75] Inventor: Stephen G. Davies, Oxford, England

[73] Assignee: The British Petroleum Company p.l.c., London, England

[21] Appl. No.: 694,567

[22] Filed: May 2, 1991

[30] Foreign Application Priority Data

May 9, 1990 [GB] United Kingdom ............... 9010383
Jul. 21, 1990 [GB] United Kingdom ............... 9016060
Nov. 30, 1990 [GB] United Kingdom ............... 9026084

[51] Int. Cl.$^5$ ................... C07D 235/02; C07D 233/32
[52] U.S. Cl. ............................ 548/302.7; 548/322.5; 548/323.5; 548/325.1; 548/325.5; 548/316.4
[58] Field of Search ............... 548/302, 317, 320, 321, 548/322

[56] References Cited

U.S. PATENT DOCUMENTS 2,441,935  8/1948  Duschinsky ..................... 548/317
2,993,906  7/1961  Sprenger et al. ................ 548/317
3,058,849  10/1992 Bakke ............................ 548/317

FOREIGN PATENT DOCUMENTS 0069445  4/1982  European Pat. Off.
0308744  9/1988  European Pat. Off.

OTHER PUBLICATIONS

Journal of Medicinal Chemistry, vol. 14, No. 2, Feb. 1971, pp. 138–144, Washington, D.C. U.S.; M. H. Hussain et al.: "Centrally Acting Cyclic Urea, Thiourea and Their N,N'-Dialkyl Derivatives, Structure–Activity Correlations" *The Whole Document*.
Fehr et al., JACS 1988, vol. 110, pp. 6909–6911.
Pauling et al., Chemical Abstracts, vol. 105 Abst. No. 78765 (1986).

Primary Examiner—Joseph Paul Brust
Assistant Examiner—Mary Susan H. Gabilan
Attorney, Agent, or Firm—Brooks, Haidt, Haffner & Delahunty

[57] ABSTRACT

Chiral imidazolidones and imidazolidinethiones having the general formula:

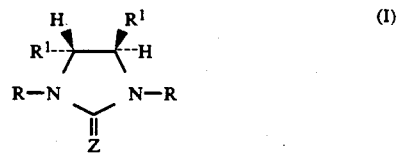

where
(a) Z is either oxygen or sulphur
(b) the R groups are independently selected from hydrogen or $R^2CO$ where $R^2$ is $C_1$ to $C_{10}$ alkyl, $C_2$ to $C_{10}$ alkenyl or benzyl and
(c) the two $R^1$ groups are either (1) identical groups selected from $C_1$ to $C_{10}$ alkyl, phenyl or $C_1$ to $C_6$ alkyl or alkoxy substituted phenyl or (2) such that together they form an alkylene group of formula $-(CH_2)_n-$ where $n=3$ to 8.

Most preferred are those compounds where both R groups are $R^2CO$ and there is a $C_2$ axis of symmetry running along the CZ double bond. Compounds of formula (I) where at least one R group is $R^2CO$ are efficient chiral auxiliaries for a range of asymmetric electrophilic substitution reactions when used in homochiral form. As such they are important tools for synthesising a range of chiral pharmaceuticals, agrochemicals and the like.

6 Claims, No Drawings

CHIRAL AUXILIARIES AND THEIR USE IN THE SYNTHESIS OF CHIRAL MOLECULES

The present invention relates to the use of chiral imidazolidinethiones and imidazolidones as chiral auxiliaries in the synthesis of chiral molecules in single enantiomeric form.

The concept of using a chiral auxiliary in the selective synthesis of single enantiomers of chiral molecules is now well established. In general terms, the chiral auxiliary comprises two parts: a reactive part having a prochiral centre where a range of chemical reactions generating a chiral centre can take place and a chiral part which directs the stereochemical course of reactions at the prochiral centre. The chiral auxiliary may be used either in single enantiomeric form or as a racemic mixture.

An example of a chiral auxiliary is the compound cyclopentadienyl iron (triphenylphosphine) carbonyl propionyl $C_pFe\ (PPh_3)(CO)COCH_2CH_3$. In this example, the methylene carbon of the propionyl group is a prochiral centre at which asymmetric electrophilic substitution can occur. It is found that the $C_pFe(PPh_3)CO$ moiety, which contains a chiral centre at the iron atom, directs any such asymmetric electrophilic substitution towards one of the two possible enantiomers formable at the prochiral centre with high selectivity. Once the new chiral centre has been created substantially in single enantiomeric form, a moiety containing the centre can be separated from the $C_pFe(PPh_3)CO$ moiety and used as desired.

Other classes of chiral auxiliary have been reported in the literature. Thus, J. Chem Soc Chem Comm 1418 (1985) describes the use of certain chiral 1,3-oxazolidone-2-thiones whilst Tetrahedron 45 1501 (1989) teaches that optically active glycerol derivatives can be produced by a synthetic method employing as a key step the reaction of an alkyl halide with the enolate of a single enantiomer of 2-methyl,5-benzoxyacetyl-4-methyl-5-phenylimidazolidine.

In addition to the above, J Org Chem 42 3776 (1977) discloses inter alia 1,3-diacetyl derivatives of 4-methyl,5-(4-carboxybutyl) imidazolidones as part of an investigation into the biosynthetic conversion of dethiobiotin to biotin.

One inherent disadvantage of the approach in general and most of the chiral auxiliaries used to date in particular is that a heavy chiral fragment has to be carried through the steps constituting the asymmetric synthesis. In practice this means that on a mole for mole basis, relatively large weights of the auxiliary have to be used. It is an object of the present invention therefore to provide new chiral auxiliaries whose mass is reduced as far as possible within the limits of providing high stereo control.

A new class of low molecular weight acyl substituted trans 4,5-disubstituted imidazolidones has now been discovered which can function as particularily efficient chiral auxiliaries.

According to the present invention there is provided compounds having the general formula:

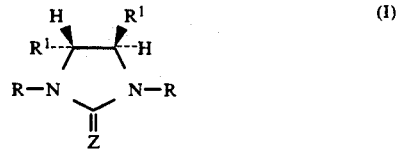

wherein
(a) Z is either oxygen or sulphur
(b) the R groups are independently selected from hydrogen or $R^2CO$ where $R^2$ is selected from $C_1$ to $C_{10}$ alkyl, $C_2$ to $C_{10}$ alkenyl or benzyl and
(c) the two $R^1$ groups are either (1) identical groups selected from $C_1$ to $C_{10}$ alkyl, phenyl or $C_1$ to $C_6$ alkyl or alkoxyl substituted phenyl or (2) such that together they form an alkylene group of formula $-(CH_2)_n-$ where n=3 to 8.

Of the compounds defined above, preferred examples are those where the $R^1$ groups are selected from $C_1$ to $C_6$ alkyl, phenyl and $C_1$ to $C_3$ alkyl or alkoxy substituted phenyl or where the two $R^1$ groups together comprise a $-(CH_2)_n-$ group in which n=3 to 6. Most preferred of all are those compounds in which the $R^1$ groups are selected from phenyl, $C_1$ to $C_3$ alkyl or alkoxy substituted phenyl or where the two $R^1$ groups together comprise $-(CH_2)_4-$.

As regards the R groups, it is preferred that either at least one, preferably two, have the formula $R^2CO$ as the resulting compounds can then act as chiral auxiliaries or that both are hydrogen as the resulting compounds are important precursors. It is most preferred that both R groups are the same $R^2CO$ group.

The compounds of formula (I) are chiral hence each example has two enantiomeric forms. According to an embodiment of the present invention there is provided a single enantiomer of a compound of formula (I) in substantially optically pure form. Substantially optically pure form in the context of this patent means that no more than 20, preferably 10 mole % of the other enantiomer is present.

Those compounds of formula (I) wherein at least one R group is $R^2CO$ and $R^2$ is $C_1$ to $C_{10}$ alkyl, $C_2$ to $C_{10}$ 1-alkenyl or benzyl are able to act as efficient chiral auxiliaries for a range of asymmetric electrophilic substitution reactions. Accordingly, in an embodiment of the present invention there is provided a process for carrying out asymmetric electrophilic substitution alpha to the carbonyl carbon on the side chain of a compound of formula:

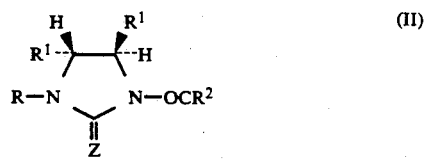

where Z, R, and $R^1$ are as defined above and $R^2$ is selected from $C_1$ to $C_{10}$ alkyl, and benzyl which comprises the steps of:
1) treating a single enantiomer of the compound of formula (II) with a metal alkyl or equivalent compound under conditions such that enolisation alpha to the carbonyl compound is caused to take place, and 2) thereafter reacting the product of step (1) with an electrophile at the carbon atom alpha to the carbonyl carbon.

The compound of formula (II) can be readily enolised by treatment with a Group IA, IIA or IIIA metal alkyl or metal alkyl halide or metal alkyl triflate at a temperature below 0° C. under an inert atmosphere. The enolate so generated is able to react with a wide range of electrophiles including alkyl halides, epoxides, aldehydes and ketones according to well known reaction schemes. The product of such reactions can be readily determined by the skilled man according to the well-known mechanistic principles set out in any standard text book of organic chemistry. Typically step (b) is also carried out below 0° C. in an inert solvent under an inert atmosphere.

In the case where $R^2$ is 1-alkenyl, the skilled man will appreciate that the $R^2CO$ group will comprise an alpha, beta unsaturated ketone which, if the carbon atom beta to the carbonyl group is prochiral, can undergo an asymmetric Michael addition with a wide range of electrophiles such a malonic ester, acetoacetic ester, amines and derived amides and the like. Such processes are typically base catalysed, e.g. by amines, alkali metal alkoxides, metal alkyls etc, and preferably are carried out below 0° C. in an inert solvent under an inert atmosphere.

Finally it will be appreciated that in the case where $R^2$ is 1-alkenyl asymmetric Diels-Alder reactions can be carried out by reacting the compound of formula (II) with an appropriate diene e.g. butadiene under for example thermal or Lewis acid catalysis.

At the end of any of the asymmetric syntheses referred to above, the newly created chiral centre can be removed from the rest of the molecule by cleaving the nitrogen-carbon bond. This can be effected by treating the product with e.g. acid, base, hydrogen peroxide, benxyl thiolate or alkoxide, e.g. methoxide, to produce an acid or ester derivative. Alternatively the product may be treated with a reducing agent such as lithium aluminium hydride in which case reductive cleavage occurs yielding an alcohol. In all such cases the precursor referred to below (R=H) is regenerated and can thereafter be reacylated.

For both the electrophilic substitution reactions and the Diels-Alder reaction mentioned above, it is most preferred that the compound employed is one having the general formula:

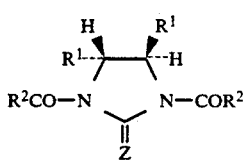

where the $R^2$ groups are identical. Such compounds which possess a $C_2$ axis of symmetry running along the CZ double bond are characterised by the fact that the prochiral sites on the two $R^2$ groups ae located in identical stereochemical environments. One consequence of this is that, for a given amount of compound, twice as much of the asymmetric reaction can take place. Thus, there is moe efficient use of the chirality in the molecule. A second and more important advantage is that by carrying out two identical asymmetric reactions, the small amounts of the minor enantiomer side product created in each asymmetric reaction are ultimately concentrated in products which are diastereoisomers of the product containing most of the major desired enantiomer.

Compounds of formula (I) where at least one R group is other than H are conveniently prepared in single enantiomeric form from single enantiomers of the corresponding precursors of formula:

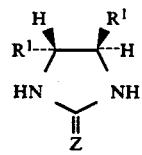

by alkylation, arylation or acylation. The techniques for carrying out these reactions will be familiar to the skilled man.

The precursor can in turn be prepared in single enantiomeric form by reacting a trans 1,2 substituted, 1,2 diamine of formula $H_2NCH(R^1)(R^1)(CH)NH_2$ with either carbonyl sulphide (Z=O) or carbon disulphide (Z=S) in the presence of acid using the method described in J Org Chem 43 1544-1546 (1978).

Alternatively, a single enantiomer of the compound of formula (I) (Z=O) can be prepared from the corresponding compound in which Z=S by treatment with mecuric acetate in an appropriate solvent.

The compounds of the present invention will find wide use in industry as reagents for synthesising a wide range of pharmaceuticals, agrochemicals and flavourings in optically pure form, thereby increasing in many cases the activity and effectiveness of the final product.

The present invention is now described with reference to the following Examples.

A. Synthesis of Imidazolidones of Formula (I)—(Z=O)

The synthesis described below starts from racemic trans 1,2-diaminocyclohexane and produces the product imidazolidones in racemic form. Single enantiomers of the product imidazolidones can be prepared by otherwise identical methods but starting from one or other of the enantiomers of trans 1,2-diaminocyclohexane. Racemic trans 1,2-diaminocyclohexane can be resolved into its constituent enantiomers by for example the methods described in U.S. Pat. No. 4,085,183.

$^1$H n.m.r data quoted below was obtained at 300 MHz in CDCl$_3$ solution.

EXAMPLE 1

Preparation of Imidazolidone of Formula (1) ($R^1$ and $R^1$=—(CH$_2$)$_4$—; R=H)

The method used is equivalent to that described in Ulrich et al, J Org Chem (1978) 43 1544.

A 50 ml round bottom, three-necked flask was charged with 10 mls of ethanol and 2.01 mls of 1,2-diaminocyclohexane. Gaseous carbonyl sulphide was introduced into the flask via a side arm and was allowed to bubble through the contents for 10 minutes. During this time, the flask became warm and the contents turned slightly yellow. The flask was allowed to cool and the contents were stirred for a further 30 minutes of ambient temperature during which time a white solid precipitated. The flask and its contents were then heated to 60° C., at which time 0.2 ml of 5M hydrochloric acid was added, and then heated to 80° C. for a further 12 hours.

After cooling, solvents were removed in vacuo and the resulting solid was extracted with 2×40 ml aliquots of chloroform. The organic layers were then combined, dried over $MgSO_4$ and then finally evaporated down to yield 1.64 g of the product (brown solid: 71%).

Properties

White crystalline solid. $^1H$ n.m.r. 4.61 (2H, bs, NH), 3.16 (2H, m, CHN), 1.97 (2H, m, Cy-C), 1.82 (2H, m, Cy-C), 1.2–1.48 (4H, m, Cy-C). Analysis C=59.69%, H=8.95% and N=20.13%.

EXAMPLE 2

Preparation of Imidazolidone of Formula (I) ($R^1$ and $R^1=-(CH_2)_4-$; R=various acyl groups)

Method 1

To a solution of 4.7 mmol of the product of Example 1 in a mixture of pydridine (12.6 mmol) and dichloromethane (20 ml) was added 14 mmol of the relevant acyl halide (RCOCl see below). The reaction mixture was then stirred at ambient for 15 hours, washed with water (2×20 ml) dried over $MgSO_4$ and then evaporated to give the desired compound.

2a: $R=CH_3CO$

White crystalline solid. $^1H$ n.m.r.=3.37 (2H, m, CHN), 2.89 (2H, m, Cy-C), 2.50 (6H, s, $COCH_3$), 1.87 (2H, m, Cy-C), 1.33–1.52 (4H, m, Cy-C).

2b: $R=C_2H_5CO$

White crystalline solid. $^1H$ n.m.r.=3.39 (2H, m, CHN), 3.04, 2.77 (4H, $ABX_3$ system, $J_{AB}$ 17.6 Hz, $J_{AX}$ 7.4 Hz, $J_{BX}$ 7.4 Hz, $COCH_2$), 2.89 (2H, m, Cy-C), 1.88 (2H, m, Cy-C), 1.33–1.53 (4H, m, Cy-C) 1.16 (6H, t, J 7.3 Hz, $CH_3$).

2c: $R=n-C_3H_7CO$

White crystalline solid. $^1H$ n.m.r.=3.38 (2H, m, CHN), 2.75–2.96 (4H, m, $COCH_2$), 2.89 (2H, m, Cy-$C_{alpha}$), 1.87 (2H, m, Cy-$C_{alpha}$), 1.62–1.73 (4H, m, $COCH_2CH_2$), 1.31–1.52 (4H, m, Cy-C), 0.98 (6H, t, J 7.4 Hz, $CH_3$).

2d: $R=i-C_3H_7CO$

White crystalline solid (43%). $^1H$ n.m.r.=3.68 (2H, septet, J 6.8 Hz, COCH), 3.41 (2H, m, CHN), 2.83 (2H, m, Cy-C), 1.88 (2H, m, Cy-C), 1.26–1.49 (4H, m, Cy-C), 1.19 (6H, d, J 6.9 Hz, $CH_3$), 1.18 (6H, d, J 6.7 Hz, $CH_3$).

2e: $R=PhCH_2CH_2CO$

White crystalline solid. $^1H$ n.m.r.=7.17–7.3 (10H, m, Ph), 3.35 (2H, m, CH-N), 3.29, 3.13 (4H, ABXY, $J_{AB}=17.2$ Hz, $J_{AX}=9.0$ Hz, $J_{BX}=6.8$ Hz, $J_{AY}=6.1$ Hz, $J_{BY}=8.3$ Hz $COCH_2CH_2Ph$), 2.99 (4H ABXY, m, $COCH_2CH_2Ph$), 2.86 (2H, m, Cy-$C_{alpha}$), 1.87 (2H, m, Cy-$C_{alpha}$), 1.27–1.5 (4H, m, Cy-$C_{Beta}$).

2f: $R=PhCH=CHCO$

White crystalline solid. $^1H$ n.m.r.=7.81, 7.55 (4H, AB, $J_{AB}=15.8$ Hz, Ph-CH=CH-CO), 7.62 (4H, m, Ph, $C_{ortho}$), 7.39 (6H, m, Ph, $C_{meta/para}$), 3.59 (2H, m, CH-N), 2.95 (2H, m, Cy-$C_{alpha}$), 1.94 (2H, m, Cy-$C_{alpha}$), 1.32–1.59 (4H, m Cy-$C_{Beta}$).

Method 2

Sodium hydride (60% dispersion in mineral oil) (24 mg, 0.6 mmol) was added to a THF solution of the product of Example 1 (30 mg, 0.21 mmol) at ambient temperature and allowed to stir for 1 hour. Propionyl chloride (0.2 ml, excess) was added and the reaction stirred for a further 3 hours before the reaction was quenched by addition of water (0.5 ml). The THF was removed in vacuo and the resulting aqueous phase extracted with dichloromethane (3×5 ml) dried over $MgSO_4$ and evaporated to give a white amorphous solid (49 mg, 81%). Although the use of prioponyl chloride is exemplified, other acyl halides can be used in an analogous fashion.

The following synthesis describes a method for producing imidazolidones of formula (I) wherein $R^1=Ph$. Again although the synthesis described employs racemic starting materials and hence produces a racemic product, the procedure applies equally to a completely homochiral synthesis.

EXAMPLE 3

Preparation of Imidazolidone of Formula (I) ($R^1=Ph$, R=H)

The procedure of Example 1 was followed except that a molar equivalent amount of cis 1,2-diamino, trans 1,2-diphenylethane was used instead of trans 1,2-diaminocyclohexane.

EXAMPLE 4

Preparation of Imidazolidone of Formula (I) ($R^1=Ph$, $R=R^2CO$)

The procedure of Example 2 was followed except that 400 mg of the product of Example 3 was used instead of the product of Example 1. The following compounds and properties were obtained using a variety of acrylating agents of formula $R^2COCl$.

4a: $R=CH_3CO$

White crystalline solid. $^1H$ n.m.r. 7.34–7.43 (6H, m, Ph, $C_{para/meta}$) 7.23–7.26 (4H, m, Ph, $C_{ortho}$), 7.23–7.26 (4H, m, Ph, $C_{ortho}$, 5.16 (2H, s, Ph-CH), 2.62 (6H, s, $COCH_3$).

4b: $R=C_2H_5CO$

White crystalline solid. $^1H$ n.m.r. 7.34–7.43 (6H, m. Ph $C_{meta/para}$), 5.16 (2H, s, Ph-CH) 3.05 (4H, q, J=7.3 Hz, $COCH_2CH_3$), 1.17 (6H, t, J=7.3 Hz $COCH_2CH_3$).

4c: $R=C_3H_7CO$

White crystalline solid. $^1H$ n.m.r. 7.34–7.42 (6H, m, Ph, $C_{meta/para}$), 7.22–7.26 (4H, m, Ph, $C_{ortho}$), 5.15 (2H, s, Ph-CH), 3.00 (4H, $ABX_2$, $J_{AB}=12.8$ Hz, $J_{AX}=7.6$ Hz, $J_{BX}=8.5$ Hz, $COCH_2$) 1.68 (4H, sextet, J=7.2 Hz, $COCH_2CH_2CH_3$), 0.96 (6H, t, J=7.4 Hz, $COCH_2CH_2CH_3$).

4d: $R=PhCH_2CH_2CO$

White crystalline solid. $^1H$ n.m.r. 7.20–7.26 (4H, m, Ph(1) $C_{ortho}$), 7.14–7.18 (4H, m, Ph(1) $C_{meta}$), 7.14–7.18 (6H, m, Ph(2) $C_{meta/para}$), 7.00–7.02 (4H, m, Ph(2), $C_{ortho}$), 6.54–6.57 (2H, m, Ph(1), $C_{para}$), 5.19 (2H, m, Ph-CH), 2.47, 2.92 (8H, $ABX_2$, $J_{AB}=0$Hz, $J_{AX}=7.7$ Hz, $J_{BX}=7.7$ Hz $COCH_2CH_2Ph$).

4e: $R=PhCH=CHCO$

White crystalline solid. $^1H$ n.m.r. 8.11 (2H, d, J=15.7 Hz COCH=), 7.84 (2H, d, J=15.7 Hz, CH-Ph), 7.65–7.69 (4H, m, Ph $C_{ortho}$), 7.34–7.45 (16H, m, Ph), 5.34 (2H, s, Ph-CH-N).

EXAMPLE 5

Alternative Synthesis of Imidazolidone of Formula (I) ($R^1=Ph$, $R=PhCH_2CH_2CO$)

To a solution of 500 mg of 1,3-di(3-phenyl propionyl)-4,5-diphenyl imidazolidinethione in 22 ml of dichloromethane was added 440 mg of mercuric acetate. The mixture was stirred at room temperature for 18 hours, filtered through celite and the procedure repeated with a further 180 mg of mercuric acetate. The product after the second treatment was filtered through celite/silica, dried over MgSO$_4$ and evaporated to yield 428 mg of the desired product as a white solid (yield 88%, see Example 4d above for $^1$H n.m.r. details).

The 1,3-di(3-phenyl propionyl)-4,5,-trans di phenylimidazolidone was prepared in two steps from cis 1,2-diamino-trans-1,2-diphenylethane using the procedure of Examples 3 and 4d with the difference that in the procedure of Example 3 carbon disulphide was used instead of carbonyl sulphide.

B. Use of Imidazolidones of Formula (I) (R=R$^2$CO) as Chiral Auxiliaries for Asymmetric Alkylation Reactions

EXAMPLE 1

Asymmetric Alkylation of the product of Example 2e with Methyl Iodide

The enolate of the product of Section A, Example 2e was prepared by adding 350 mg of the product to 2 mls of sodium bis (trimethylsilyl)amide at −78° C. and stirring the resulting mixture for 90 minutes. At the end of this time, 0.25 ml of methyl iodide was added and stirring continued. After a further 4 hours the mixture was warmed to −30° C. and stirring continued for a further 15 hours. Thereafter, the mixture was brought to room temperature and the products isolated by crystallisation from ethanol.

Properties of Alkylated Product

White crystalline solid. $^1$H n.m.r.-7.19–7.31 (10H, m, Ph), 3.96 (2H, q of t, J=7.0 Hz, 8.6 Hz, COCH), 3.36 (2H, m, CH—N), 2.85 (2H, m, Cy-C$_{alpha}$), 2.57, 3.19 (4H ABX, J$_{AB}$=13.4 Hz, J$_{AX}$=5.9 Hz, J$_{BX}$=8.5 Hz, PhCH$_2$—), 1.87 (2H, m Cy-C$_{alpha}$), 1.2–1.48 (4H, m, Cy-C$_{Beta}$), 1.14 (6H, d, J=7.0 Hz CH$_3$).

EXAMPLE 2

Asymmetric Alkylation of the product of Example 2b with Benzyl Bromide

The procedure of Example 1 was repeated except that the product of Section A, Example 2b and benzyl bromide were used where appropriate.

Properties of Product

White crystalline solid. $^1$H n.m.r.=7.14–7.31 (10H, m, Ph), 3.92 (2H, sextet, J=6.8 Hz, COCH), 2.98 (2H, m, CH-N), 2.74, 2.93 (4H, ABX, J$_{AB}$=13.3 Hz, J$_{AX}$=8.4 H$_2$, J$_{BX}$=6.7 Hz CH$_2$Ph), 2.65 (2H, m, Cy-C$_{alpha}$), 1.76 (2H, m, Cy-C$_{alpha}$) 1.24–1.41 (4H, m, Cy-C$_{Beta}$), 1.21 (6H, d, J=6.7 Hz, CH$_3$).

C. Use of Imidazolidones of Formula (I) (R=R$^2$CO) as Chiral Auxiliaries for Asymmetric Aldol Condensations

EXAMPLE 1

Asymmetric Aldol Condensation between Benzaldehyde and the product of Section A, Example 2b 222 mg of the product of Section A, Example 2b was dissolved in 8 ml of dichloromethane at ambient temperature. Immediately afterwards a small amount of dry molecular sieve was added. The reaction mixture was then degassed and placed under a nitrogen atmosphere in a Schlenk tube protected by a calcium chloride guard tube fitted in the line.

After cooling the reaction mixture to −5° C., 2 ml of a 1 molar solution of dibutyl boron triflate in dichloromethane was added with stirring. N-ethylpiperidine (245 mg in 2 ml dichloromethane) was then added and the mixture cooled to −78° C. As soon as 15 minutes at −78° C. had elapsed, a solution of 215 mg of benzaldehyde in 2 ml dichloromethane was added dropwise over 5 minutes whilst maintaining the reaction mixture at −78° C.

A further sixty minutes was allowed to elapse after which the mixture was warmed to 0° C. and allowed to stir for a further sixty minutes. Thereafter a quenching solution of a mixture of pH7 phosphate buffer (2 ml) and methanol (2 ml) were added after which a mixture of 2 mls of 30% H$_2$O$_2$ and 2 ml of methanol were added over a period of an hour. During this final addition the reaction mixture was maintained at 0°–5° C.

The volatile components were removed on a rotary evaporator and the residue extracted with ether (3×10 ml), combined, washed with 5% aqueous sodium bicarbonate and then dried over MgSO$_4$. Solvent evaporation afforded crude product (white solid) which was mainly product together with a small amount of unreacted benzaldehyde. Chromatography on silica (ethyl acetate) yield two products, one diastereoisomer of the dialdol product R=R=PhCH(OH)CH(CH$_3$)CO and a small amount (ca 8%) of the monoaldol product R=PhCH(OH)CH(CH$_3$)CO, R=CH$_3$CH$_2$CO). The dialdol product recrystallised from ethanol had the following properties. White crystalline solid. $^1$H n.m.r.=7.26–7.45 (10H, m, Ph), 5.24 (2H, m, CH(OH)), 4.04 (2H, q of d, J=7.2 Hz, 2.8 Hz COCH), 3.44 (2H, m, CH-N), 3.27 (2H, d, J=2.2 Hz, OH), 2.88 (2H, m, Cy-C$_{alpha}$), 1.92 (2H, m, Cy-C$_{alpha}$), 1.33–1.57 (4H, m, Cy-C$_{Beta}$), 1.12 (6H, d, J=7.2 Hz, CH$_3$).

D. Synthesis of Imidazolidinethiones of Formula (I)-(Z=S)

EXAMPLE 1

Preparation of Imidazolidinethione of Formula (I) (R$^1$ and R$^1$=(CH$_2$)$_4$; R=H)

14 mls of carbon disulphide was slowly added to 24 ml (0.2 mol) of 1,2-diaminocyclohexane in 100 ml of solvent (water:ethanol (1:1)) over a period of 1 hour. Addition of ca 25% of the carbon disulphide caused the reaction temperature to rise from ambient to 60° C. and the reaction was then externally heated at this temperature during the remainder of the addition to avoid precipitation of product. After addition, the reaction was heated under reflux for 1 hour, acidified with 10% HCL (2 ml) and then refluxed for a further 9 hours. The reaction mixture was then allowed to cool and the solid precipitate collected and washed with 25 ml cold ethanol. 24.16 g (77%) of the desired product was obtained as a white crystalline solid.

$^1$H nmr (delta): 6.24 (2H, bs, NH), 3.31 (2H, m, CHN), 2.06 (2H, m, Cy-C), 1.84 (2H, m, Cy-C), 1.53 (2H, m, Cy-C), 1.34 (2H, m, Cy-C).

EXAMPLE 2

Preparation of Imidazolidinethione of Formula (I) (R$^1$=phenyl; R=H)

The procedure described in Example 1 was followed except that 2 ml of carbon disulphide was used and the 1,2-diaminocyclohexane was replaced by stilbene.diamine 4.25 g (67%) of the desired product was obtained as a white crystalline solid. $^1$H nmr (delta): 7.39 (6H, m, Ph(para/meta)), 7.29 (4H, m, Ph(ortho)), 6.41 (2H, bs, NH), 4.82 (2H, s, PhCH).

EXAMPLE 3

Preparation of Imidazolidinethione of formula (I) $R^1$ and $R^1$ together=$(CH_2)_4$; R=various acyl groups)

a. $R=CH_3CO$ 14 mmol of acetyl chloride was added to a solution of the product of Example 1 (4.7 mmol) in pyridine (12.6 mmol) in dichloromethane (20 ml) at room temperature. The reaction mixture was stirred for 15 hours, washed with water (2×20 ml) dried over magnesium sulphate and then evaporated to give the desired compound (78% yield).

b. $R=C_2H_5CO$

The procedure of Example 3a. was repeated except that propionyl chloride replaced acetyl chloride. A 86% yield of desired product was obtained.

c. $R=C_3H_7CO$

The procedure of Example 3a. was repeated except that butanoyl chloride replaced acetyl chloride. A 70% yield of desired product was obtained.

d. R=cinnamoyl

The procedure of Example 3a was followed except that cinnamoyl chloride replaced acetyl chloride. A 72% yield of the desired product was obtained.

EXAMPLE 4

Preparation of Imidazolidinethione of formula (I) ($R^1$=Ph; R=various acyl groups)

a. $R=CH_3CO$

The procedure of Example 3a. was followed except that 4.7 mmol of the product of Example 2 replaced the product of Example 1. A 94% yield of desired product was obtained.

b. $R=C_2H_5CO$

The procedure of Example 4a. was followed except that propionyl chloride replaced acetyl chloride. A 88% yield of desired product was obtained.

c. $R=C_3H_7CO$

The procedure of Example 4a. was followed except that butanoyl chloride replaced acetyl chloride. An 88% yield of desired product was obtained.

The $^1H$ nmr data (delta) for the products of Examples 3a-d and Examples 4a-c were found to be as follows.

3 a. 3.50 (2H, m, CHN), 2.76 (2H, m, Cy-$C_a$), 2.74 (6H, s, $COCH_3$), 1.89 (2H, m, Cy-$C_a$), 1.46 (2H, m, Cy-$C_b$), 1.31 (2H, m, Cy-$C_b$).

3 b. 3.51 (2H, m, CHN), 3.42, 2.96 (4H, $ABX_3$ system, $J_{AB}$ 16.7 Hz, $J_{AX}$ 7.4 Hz, $J_{BX}$ 7.2 Hz, $COCH_2$), 2.67 (2H, m, Cy-$C_a$), 1.88 (2H, m, Cy-$C_a$), 1.45 (2H, m, Cy-$C_b$), 1.30 (2H, m, Cy-$C_b$), 1.21 (6H, t, J 7.3 Hz, $CH_3$).

3 c. 3.50 (2H, m, CHN), 3.23, 3.08 (4H, ABMX system, $J_{AB}$ 16.1 Hz, $J_{AM}$ 8.1 Hz, $J_{AX}$ 6.4 Hz, $J_{BM}$ 7.0 Hz, $J_{BX}$ 7.0 Hz), 2.68 (2H, m, Cy-$C_a$), 1.89 (2H, m, Cy-$C_a$), 1.74 (4H, m, $COCH_2CH_2$), 1.45 (2H, m, Cy-$C_b$), 1.28 (2H, m, Cy-$C_b$), 0.97 (6H, t, J 7.4 Hz, $CH_3$).

3 d. 7.68, 7.54 (4H, AB system, J 15.7 Hz, PhCH=CHCO—), 7.57 (4H, m, Ph(ortho)), 7.39 (6H, m, Ph(para/meta)), 3.72 (2H, m, CHN), 2.76 (2H, m, Cy-C), 1.95 (2H, m, Cy-C), 1.42-1.52 (4H, m, Cy-C).

4 a. 7.39 (6H, m, Ph(para/meta)), 7.25 (4H, m, Ph(ortho)), 5.39 (2H, s, PhCH), 2.88 (6H, s, $CH_3$).

4 b. 7.39 (6H, m, Ph(para/meta)), 7.29 (4H, m, Ph(ortho)), 5.38 (2H, s, PhCH), 3.43, 3.31 (4H, $ABX_3$ system, $J_{AB}$ 18.2 Hz, $J_{AX}$ 7.1 Hz, $J_{BX}$ 7.2 Hz, $COCH_2$), 1.15 (6H, t, J 3.7 Hz, $CH_3$).

4 c. 7.33-7.42 (6H, m, Ph(para/meta)), 7.22-7.26 (4H, m, Ph(ortho)), 5.36 (2H, s, PhCH), 3.27, 3.35 (4H, ABMX system, $J_{AB}$ 17.0 Hz, $J_{AM}$ 8.1 Hz, $J_{AX}$ 6.5 Hz, $J_{BM}$ 8.0 Hz, $J_{BX}$ 6.7 Hz), 1.68 (4H, m, $COCH_2CH_2$), 0.93 (6H, t, J 7.4 Hz, $CH_3$).

Examples 3 and 4 are illustrative of methods of acylating 4,5-transcyclohexylimidazolidmethione and 3,4-diphenylimidazolidimethione. The yields obtained in the examples can be further improved by optimising the relative amounts of reactants and by employing catalytic amounts of 4-(dimethylamino)pyridine.

EXAMPLE 5

Alternative Preparation of Imidazolidinethione of Formula (I) ($R^1$ and $R^1$ together=$(CH_2)_4$; R=H)

Trans-1,2-diaminocyclohexane (6.0 ml, 50 mmol), water (12 ml) and ethanol (12 ml) were placed in a 100 ml round bottom flask fitted with a reflux condenser and with a pessure-equalising dropping funnel on top of that. The apparatus was placed in an oil-bath and the dropping funnel was charged with carbon disulphide (3.5 ml, 58.2 mmol). Approximately 20% of the carbon disulphide was added causing a rapid exothermic reaction. The oilbath was then heated to 80° C. and the remainder of the carbon disulphide added dropwise ensuring that the product did not start precipitating out of solution. At the end of the addition the reaction was heated at reflux for 1 hour and then acidified with 5.0N hydrochloric acid (0.5 ml) and allowed to reflux for 12 hours. On cooling, the desired product precipitated out from solution and could be collected by filtration. Washing with a little cold ethanol removed some of the beige colour and gave the product as a white fluffy solid (7.32 g, 94%). Analysis: C=53.85%, H=7.79%, N=17.89%.

EXAMPLE 6

Alternative Preparation of Imidazolidinethione of Formula (I) ($R^1$=Ph; R=H)

Stilbene diamine (cis-1,2-diphenyl-trans-1,2-diaminoethane) (21.2 g, 100 mmol) was reacted with carbon disulphide (7.0 ml, 116 mmol) in a water-ethanol solvent system (1:1-100 ml) under identical conditions to those described in Example 5 to give 4,5-diphenylimidazolidinethione as a cream solid (22.90 g, 90%), m.p. 212°-214° C. (Analysis; C, 71.08%; H, 5.51%; N, 11.36%.

EXAMPLE 7

Preparation of Imidazolidinethione of Formula (I) ($R^1$ and $R^1$ together=$(CH_2)_4$; R=H)-RR enantiomer In a manner entirely analogous to Example 5, (R,R)-trans-1,2-diaminocyclohexane (824 mg, 7.22 mmol) was reacted with carbon disulphide (0.55 ml, 9.11 mmol) in a mixture of water (2 ml) and ethanol (2 ml). At the end of the reaction, the precipitate was collected by filtration (661 mg), evaporated to dryness, triturated with dichloromethane (2×20 ml) and the resulting organic solution evaporated down to a white solid (141 mg). The combined yield of product was thus 802 mg (71%); all spectroscopic data was in agreement with that obtained from racemic samples, $[alpha]_D^{20}=+54.2°$ (c=1.10/$CHCl_3$).

EXAMPLE 8

Preparation of Imidazolidinethione of Formula (I)
($R^1$=Ph; R=H)-RR enantiomer

In a manner entirely analogous to Example 6 (R,R)-stilbene diamine (4.20 g, 19.8 mmol) was reacted with carbon disulphide (1.45 ml, 24.0 mmol) in a mixture of water (10 ml) and ethanol (10 ml). At the end of the reaction, the precipitate was collected by filtration to give the product as cream needles, (3.64 g, 71%); all spectroscopic data was in agreement with that obtained from racemic samples, $[alpha]_D^{20}=65°$ (c=0.25/CHCl$_3$).

EXAMPLE 9

Preparation of Imidazolidinethione of Formula (I) ($R^1$ and $R^1$ together=(CH$_2$)$_4$; R=CH$_3$CH$_2$CO)-RR enantiomer 700 mg (4.48 mmol) of the product of Example 7 was treated with pyridine (0.9 ml, 11.1 mmol) and propionyl chloride (1.2 ml, 13.8 mmol) in dichloromethane (15 ml) in the presence of a catalytic amount of 4-(dimethylamino)pyridine. The desired product was obtained after stirring for 12 hours at ambient temperature and chromatography through a short plug of silica gel (981 mg, 82%) $[alpha]_D^{20}= -183°$ (c=0.3/CHCl$_3$).

EXAMPLE 10

Preparation of Imidazolidinethione of Formula (I) ($R^1$=Ph; R=CH$_3$CH$_2$CO)-RR enantiomer The procedure of Example 9 was followed except that 199 mg (0.78 mmol) of the product of Example 8 was used together with 0.15 ml (1.86 mmol) of pyridine, 0.4 ml (4.6 mmol) of propionyl chloride and 5 ml of dichloromethane. A yield of 161 mg (56%) of desired product was obtained.

E. Synthesis of Imidazolidones of Formula (I) (Z=O) from the corresponding Imidazolidinethiones of Formula (I) (Z=S)

EXAMPLE 1

(Formula (I) $R^1$ and $R^1$=(CH$_2$)$_4$; R=various acyl groups)

(a) R=CH$_3$CO

To a solution of 1,3-diacetyl-4,5-transcyclohexylimidazolidine thione (500 mg, 2.08 mmol) in dichloromethane (10 ml) at ambient temperature was added mercury (II) acetate (750 mg, 2.35 mmol). The reaction was allowed to stir for 12 hours before the reaction mixture was filtered through celite (washed with dichloromethane) and then stirred with fresh mercury (II) acetate (350 mg, 1.10 mmol) for 12 hours more. At the end of this second period, the reaction mixture was filtered through celite, dried over MgSO$_4$ and evaporated down to a cream solid. As this solid could not be readily purified by recrystallisation it was sublimed in vacuo (s.p. 60° C./0.7 mmHg) to give the corresponding imidazolidone as a white crystalline solid, (356 mg, 76%).

(b) R=CH$_3$CH$_2$CO

In an analogous manner to that described in (a) above, treatment of 1,3-dipropionyl-4,5-transcyclohexylimidazolidinethione (24.5 g, 91.3 mmol) with two batches of mercury (II) acetate (29.8 g, 93.5 mmol) and 11.2 g, (35.1 mmol) in dichloromethane (2×200 ml) gave a cream solid. Chromatography through a short plug of silica gel (eluting with dichloromethane) gave the corresponding imidazolidone as a white crystalline solid (20.32 g, 88%).

(c) R=CH$_3$(CH$_2$)$_2$CO

In an analogous manner to that described in (a) above, treatment of 1,3-dibutanoyl-4,5-transcyclohexylimidazolidinethione (7.75 g, 26.1 mmol) with two batches of mercury (II) acetate (9.0 g, 28.2 mmol and 1.50 g, 4.7 mmol) in diethyl ether (2×75 ml) gave a cream solid. Chromatography through a short plug of silica (eluting with dichloromethane) gave the corresponding imidazolidone as a white crystalline solid (5.13 g, 70%).

(d) R=Cinnamoyl

In an analogous manner to that described in (a) above, treatment of 1,3-di(3-phenylpropionyl)-4,5-transcyclohexyl imidazolidinethione (2.00 g, 4.76 mmol) with two batches of mercury (II) acetate (2.00 g, 6.28 mmol and 0.80 g, 2.51 mmol) in dichloromethane (2×50 ml) gave a cream solid. Chromatography through a short plug of silica (eluting with dichlormethane) gave the corresponding imidazolidone as a white crystalline solid (1.58 g, 82%).

EXAMPLE 2

(Formula (I) $R^1$=(Ph; R=various acyl groups)

(a) R=CH$_3$CO

In an analogous manner to that described in Example 1(a) above, treatment of 1,3-diacetyl-4,5-diphenylimidazolidinethione (501 mg, 1.48 mmol) with two batches of mercury (II) acetate (550 mg, 1.73 mmol and 200 mg, 0.63 mmol) in dichloromethane (2×25 ml) gave a cream solid. Chromatography through a short plug of silica (eluting with dichloromethane) gave the corresponding imidazolidone as a white crystalline solid, (444 mg, 93%).

(b) R=CH$_3$CH$_2$CO

In an analogous manner to that described in Example 1(a) above, treatment of 1,3-dipropionyl-4,5-diphenylimidazolidinethione (3.80 g, 10.4 mmol) with two batches of mercury (II) acetate (4.80 g, 15.1 mmol and 1.20 g, 3.80 mmol) in dichloromethane (2×50 ml) gave a cream solid. Chromatography through a short plug of silica (eluting with dichloromethane) gave the corresponding imidazolidone as a white crystalline solid, (3.30 g, 91%).

(c) R=CH$_3$(CH$_2$)$_2$CO

In an analogous manner to that described in Example 1(a) above, treatment of 1,3-dibutanoyl-4,5-diphenylimidazolidinethione (3.15 g, 8.00 mmol) with two batches of mercury (II) acetate (3.55 g, 10.5 mmol and 1.10 g, 3.45 mmol) in dichloromethane (2×75 ml) gave an oily solid. Chromatography through a short plug of silica (eluting with dichloromethane) gave the corresponding imidazolidone as a white crystalline solid, (2.6 g, 87%).

EXAMPLE 3

(Formula (I) $R^1$ and $R^1$=(CH$_2$)$_4$; R=CH$_3$CH$_2$CO, RR enantiomer)

In an analogous manner to that described in Example 1(a) above, treatment of (R,R)-1,3-dipropionyl-4,5-transcyclohexylimidazolidine thione (950 mg, 3.54 mmol) with two batches of mercury (II) acetate (1.10 g, 3.45 mmol and 320 mg, 1.00 mmol) in dichloromethane (2×35 ml) gave a white amorphous solid (871 mg, 98%). Chromatography through a short plug of silica (eluting with dichloromethane) gave the corresponding imidazolidone as a white crystalline solid, (773 mg, 87%), $[alpha]_D^{20} = -151.3°$ (c=0.23/CHCl3).

EXAMPLE 4

(Formula (I) $R^1$=Ph; R=CH3CH2CO; RR enantiomer)

In an analogous manner to that described in Example 1(a) above, treatment of (R,R)-1,3-dipropionyl-4,5-diphenylimidazolidinethione (161 mg, 0.44 mmol) with two batches of mercury (II) acetate (154 mg, 0.48 mmol and 60 mg, 0.19 mmol) in dichloromethane (2×5 ml) gave the corresponding imidazolidone as a white amorphous solid, after chromatography through a short plug of silica (eluting with dichloromethane), (122 mg, 79%), $[alpha]_D^{20} = -101.5°$ (c=1.00/CHCl3).

I claim:

1. Compounds having the formula:

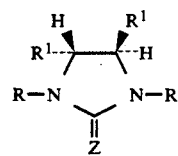

wherein
(a) Z is either oxygen or sulphur
(b) the R groups are independently selected from hydrogen or $R^2CO$ where $R^2$ is selected from $C_1$ to $C_{10}$ alkyl, $C_2$ to $C_{10}$ alkenyl or benzyl and
(c) the two $R^1$ groups are oriented trans and are either (1) identical groups selected from $C_1$ to $C_{10}$ alkyl, phenyl, or $C_1$ to $C_6$ alkyl or alkoxy substituted phenyl or (2) such that together they form an alkylene group of formula —$(CH_2)_n$— where n=3 to 8.

2. Compounds as claimed in claim 1 wherein the R groups are identical $R^2CO$ groups.

3. Compounds as claimed in claim 1 wherein the two $R^1$ groups are either (1) selected from $C_1$ to $C_6$ alkyl, phenyl or $C_1$ to $C_3$ alkyl or alkoxy substituted phenyl or (2) such that together they form —$(CH_2)_n$— where n=3 to 6.

4. Compounds as claimed in claim 3 wherein either both $R^1$ groups are phenyl or where both $R^1$ groups together form —$(CH_2)_4$—.

5. Compounds as claimed in claim 1 wherein both R groups are hydrogen.

6. Compounds as claimed in claim 1 in substantially optically pure form.

* * * * *